(12) United States Patent
Williamson

(10) Patent No.: US 7,920,920 B1
(45) Date of Patent: Apr. 5, 2011

(54) ALGORITHM FOR CAPTURE DETECTION

(75) Inventor: Richard Williamson, Saugus, CA (US)

(73) Assignee: Pacesetter, Inc., Sylmar, CA (US)

( * ) Notice: Subject to any disclaimer, the term of this patent is extended or adjusted under 35 U.S.C. 154(b) by 1252 days.

(21) Appl. No.: 11/469,420

(22) Filed: Aug. 31, 2006

(51) Int. Cl.
*A61N 1/00* (2006.01)

(52) U.S. Cl. ........................................ 607/28

(58) Field of Classification Search ............... 607/27–28
See application file for complete search history.

(56) References Cited

U.S. PATENT DOCUMENTS

| | | | |
|---|---|---|---|
| 5,466,254 A | 11/1995 | Helland | |
| 6,731,985 B2 | 5/2004 | Poore et al. | |
| 6,810,284 B1 * | 10/2004 | Bradley | 600/510 |
| 6,850,704 B1 * | 2/2005 | Dave | 398/2 |
| 7,139,611 B1 * | 11/2006 | Kroll et al. | 607/28 |
| 2001/0049543 A1 * | 12/2001 | Kroll | 607/28 |
| 2003/0050671 A1 * | 3/2003 | Bradley | 607/27 |
| 2003/0083708 A1 | 5/2003 | Bradley et al. | |
| 2003/0195579 A1 * | 10/2003 | Bradley et al. | 607/27 |

FOREIGN PATENT DOCUMENTS

| | | |
|---|---|---|
| EP | 1291038 A2 | 3/2003 |
| EP | 1302217 A2 | 4/2003 |
| EP | 1291038 A3 | 1/2005 |
| EP | 1302217 A3 | 1/2005 |

\* cited by examiner

*Primary Examiner* — Mark W Bockelman
*Assistant Examiner* — Roland Dinga

(57) ABSTRACT

An exemplary method includes receiving a signal of cardiac electrical activity after delivery of electrical energy to the heart, rectifying the signal to produce a rectified signal, comparing the rectified signal to the signal and, based at least in part on the comparing, deciding whether the delivered electrical energy resulted in non-capture, capture or fusion. Various other exemplary methods, devices, systems, etc., are also disclosed.

12 Claims, 11 Drawing Sheets

Additional Information
800

Table 910

|  | Rectified PDI ≥ Threshold | Rectified PDI < Threshold |
|---|---|---|
| Non-rectified PDI ≥ Threshold | Capture | NA |
| Non-rectified PDI < Threshold | Fusion | Non-capture |

Table 920

|  | $D_{MAX}$ ≥ Threshold | $D_{MAX}$ < Threshold |
|---|---|---|
| Non-rectified PDI ≥ Threshold | Capture | NA |
| Non-rectified PDI < Threshold | Fusion | Non-capture |

Fig. 9

ALGORITHM FOR CAPTURE DETECTION

TECHNICAL FIELD

Subject matter presented herein relates generally to cardiac pacing and/or stimulation therapy. Various examples concern mechanisms for capture detection.

BACKGROUND

Cardiac pacing devices typically aim to deliver pacing pulses to the heart at an energy level sufficient to cause capture without excessively draining power. For a variety of reasons, the energy level at which capture occurs may change over time. Consequently, so-called threshold search algorithms have been developed to help determine an energy level sufficient to cause capture. While such search algorithms may occur on a regular basis (e.g., daily basis), they may also be triggered by loss of capture.

To trigger a search algorithm based on loss of capture, some mechanism must be used to detect or infer loss of capture. However, conventional mechanisms can fail to discriminate fusion from loss of capture and hence may trigger a search where a search is not needed. Searches expend power and may not be well tolerated by some patients. Further, cardiac resynchronization therapy (CRT), which may rely on bi-ventricular pacing, can offer more opportunities for loss of capture. Yet further, a search can disturb CRT.

As described herein, exemplary mechanisms aim to increase accuracy of loss of capture detections or inferences. In addition, various exemplary mechanisms aim to distinguish fusion. Such mechanisms can allow for more consistent CRT therapy and help prevent unnecessary threshold searches. Various exemplary mechanisms described herein aim to satisfy these and/or other needs.

SUMMARY

An exemplary method includes receiving a signal of cardiac electrical activity after delivery of electrical energy to the heart, rectifying the signal to produce a rectified signal, comparing the rectified signal to the signal and, based at least in part on the comparing, deciding whether the delivered electrical energy resulted in non-capture, capture or fusion. Various other exemplary methods, devices, systems, etc., are also disclosed.

BRIEF DESCRIPTION OF THE DRAWINGS

Features and advantages of the described implementations can be more readily understood by reference to the following description taken in conjunction with the accompanying drawings.

FIG. 9 is two tables for use in deciding whether capture, non-capture or fusion occurred, based at least in part on IEGM information (e.g., analysis of such information).

DETAILED DESCRIPTION

The following description includes the best mode presently contemplated for practicing the described implementations. This description is not to be taken in a limiting sense, but rather is made merely for the purpose of describing the general principles of the implementations. The scope of the described implementations should be ascertained with reference to the issued claims. In the description that follows, like are typically numerals or reference designators will be used to reference like parts or elements throughout.

Exemplary Stimulation Device

The techniques described below are intended to be implemented in connection with any stimulation device that is configured or configurable to delivery cardiac therapy and/or sense information germane to cardiac therapy.

Figure 1:
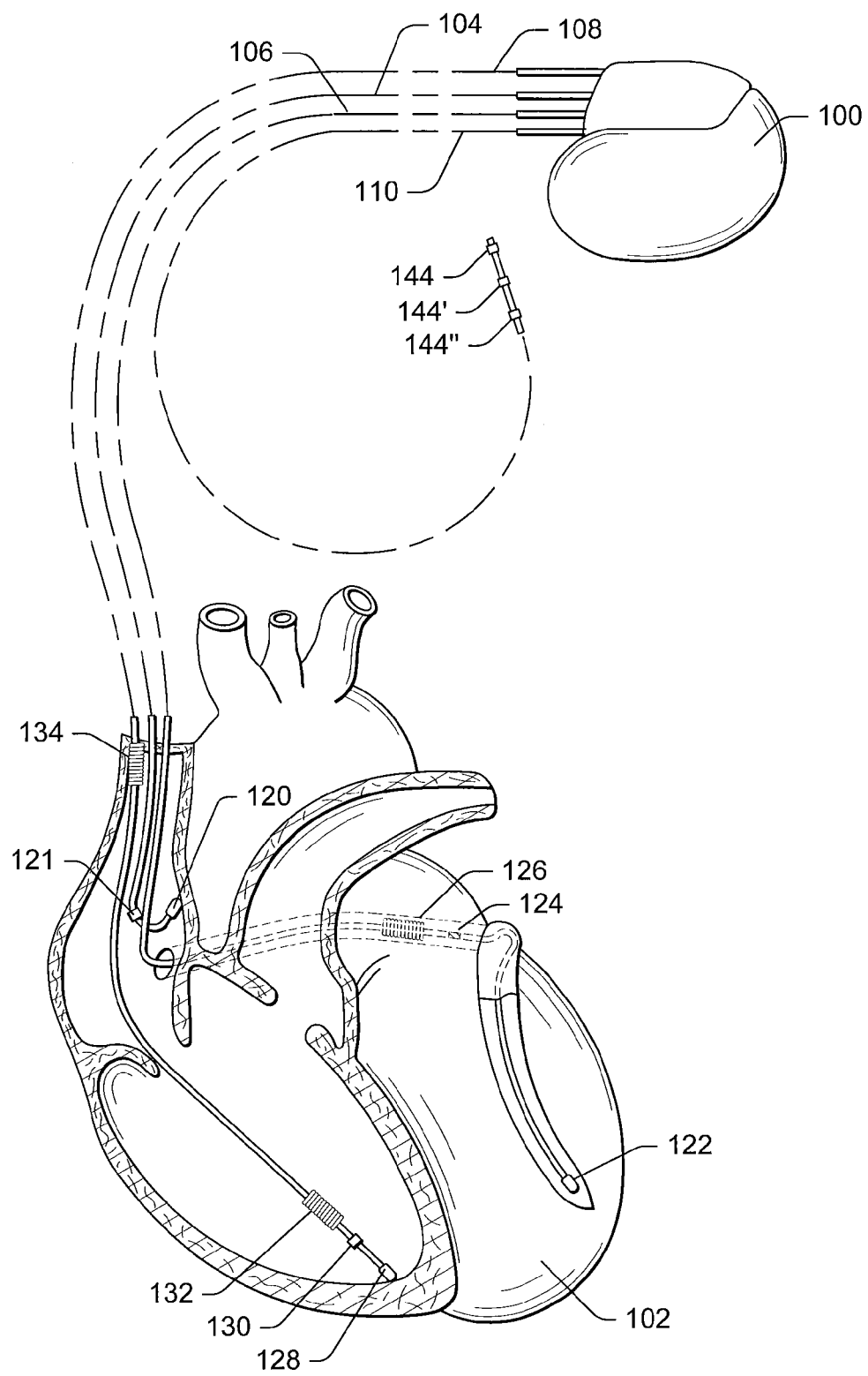
FIG. 1 is a simplified diagram illustrating an exemplary implantable stimulation device in electrical communication with at least three leads implanted into a patient's heart and at least one other lead for sensing and/or delivering stimulation and/or shock therapy. Other devices with more or fewer leads may also be suitable.

FIG. 1 shows an exemplary stimulation device 100 in electrical communication with a patient's heart 102 by way of three leads 104, 106, 108, suitable for delivering multi-chamber stimulation and shock therapy. The leads 104, 106, 108 are optionally configurable for delivery of stimulation pulses suitable for stimulation of nerves or other tissue. In addition, the device 100 includes a fourth lead 110 having, in this implementation, three electrodes 144, 144', 144" suitable for stimulation and/or sensing of physiologic signals. This lead may be positioned in and/or near a patient's heart and/or remote from the heart.

The right atrial lead 104, as the name implies, is positioned in and/or passes through a patient's right atrium. The right atrial lead 104 optionally senses atrial cardiac signals and/or provide right atrial chamber stimulation therapy. As shown in FIG. 1, the stimulation device 100 is coupled to an implantable right atrial lead 104 having, for example, an atrial tip electrode 120, which typically is implanted in the patient's right atrial appendage. The lead 104, as shown in FIG. 1, also includes an atrial ring electrode 121. Of course, the lead 104 may have other electrodes as well. For example, the right atrial lead optionally includes a distal bifurcation having electrodes suitable for stimulation and/or sensing.

To sense atrial cardiac signals, ventricular cardiac signals and/or to provide chamber pacing therapy, particularly on the left side of a patient's heart, the stimulation device 100 is coupled to a coronary sinus lead 106 designed for placement in the coronary sinus and/or tributary veins of the coronary sinus. Thus, the coronary sinus lead 106 is optionally suitable for positioning at least one distal electrode adjacent to the left ventricle and/or additional electrode(s) adjacent to the left atrium. In a normal heart, tributary veins of the coronary sinus include, but may not be limited to, the great cardiac vein, the left marginal vein, the left posterior ventricular vein, the middle cardiac vein, and the small cardiac vein.

Accordingly, an exemplary coronary sinus lead 106 is optionally designed to receive atrial and ventricular cardiac signals and to deliver left ventricular pacing therapy using, for example, at least a left ventricular tip electrode 122, left atrial pacing therapy using at least a left atrial ring electrode 124, and shocking therapy using at least a left atrial coil electrode 126. For a complete description of a coronary sinus lead, the reader is directed to U.S. Pat. No. 5,466,254, "Coronary Sinus Lead with Atrial Sensing Capability" (Helland), which is incorporated herein by reference. The coronary sinus lead 106 further optionally includes electrodes for stimulation of nerves or other tissue. Such a lead may include bifurcations or legs. For example, an exemplary coronary sinus lead includes pacing electrodes capable of delivering pacing pulses to a patient's left ventricle and at least one electrode capable of stimulating an autonomic nerve.

The stimulation device 100 is also shown in electrical communication with the patient's heart 102 by way of an implantable right ventricular lead 108 having, in this exemplary implementation, a right ventricular tip electrode 128, a right ventricular ring electrode 130, a right ventricular (RV) coil electrode 132, and an SVC coil electrode 134. Typically, the right ventricular lead 108 is transvenously inserted into the heart 102 to place the right ventricular tip electrode 128 in the right ventricular apex so that the RV coil electrode 132 will be positioned in the right ventricle and the SVC coil electrode 134 will be positioned in the superior vena cava. Accordingly, the right ventricular lead 108 is capable of sensing or receiving cardiac signals, and delivering stimulation in the form of pacing and shock therapy to the right ventricle. An exemplary right ventricular lead may also include at least one electrode capable of stimulating other tissue; such an electrode may be positioned on the lead or a bifurcation or leg of the lead.

Figure 2:
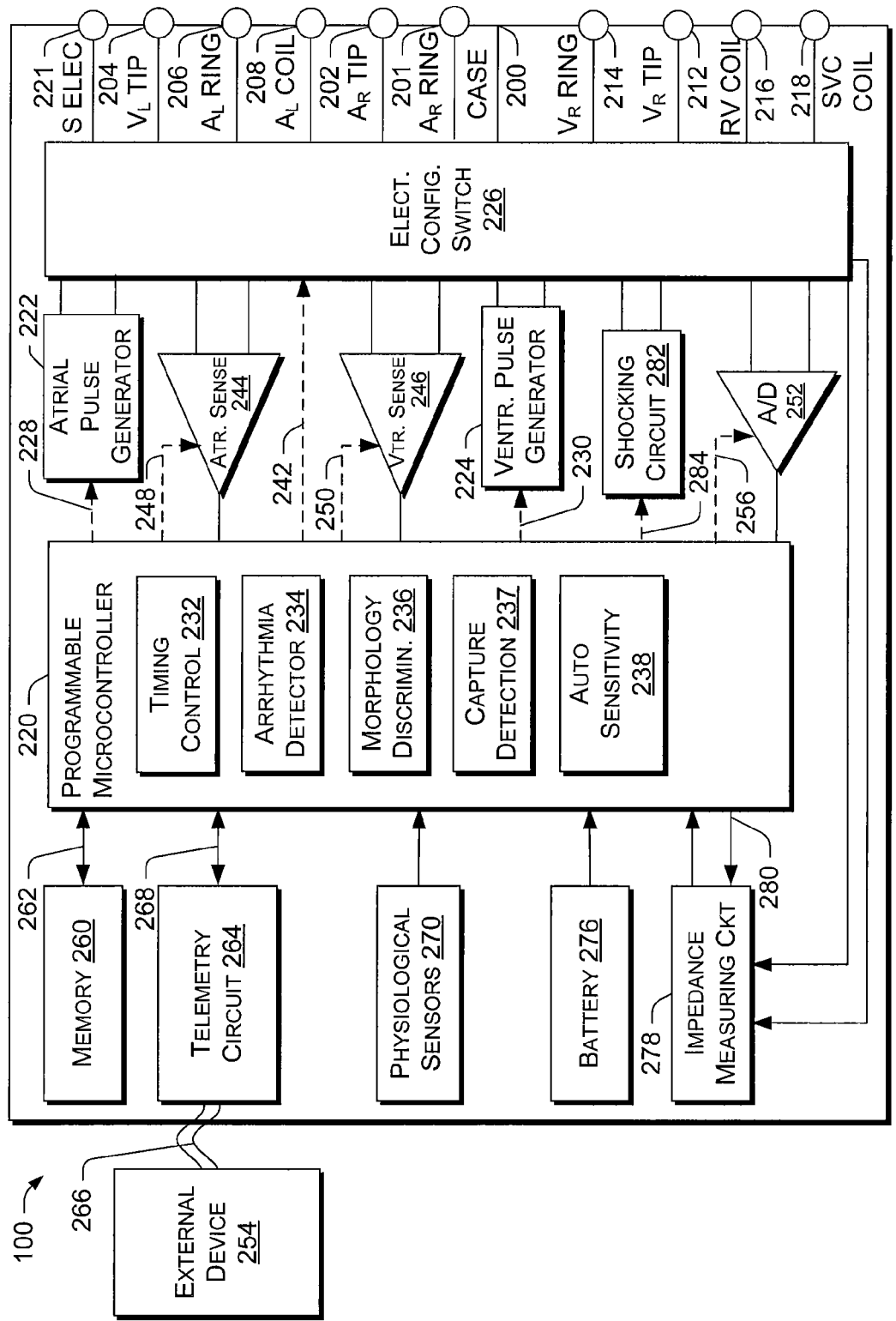
FIG. 2 is a functional block diagram of an exemplary implantable stimulation device illustrating basic elements that are configured to provide cardioversion, defibrillation, pacing stimulation and/or other tissue stimulation. The implantable stimulation device is further configured to sense information and administer therapy responsive to such information.

FIG. 2 shows an exemplary, simplified block diagram depicting various components of stimulation device 100. The stimulation device 100 can be capable of treating both fast and slow arrhythmias with stimulation therapy, including cardioversion, defibrillation, and pacing stimulation. While a particular multi-chamber device is shown, it is to be appreciated and understood that this is done for illustration purposes only. Thus, the techniques, methods, etc., described below can be implemented in connection with any suitably configured or configurable stimulation device. Accordingly, one of skill in the art could readily duplicate, eliminate, or disable the appropriate circuitry in any desired combination to provide a device capable of treating the appropriate chamber(s) or regions of a patient's heart.

Housing 200 for the stimulation device 100 is often referred to as the "can", "case" or "case electrode", and may be programmably selected to act as the return electrode for all "unipolar" modes. Housing 200 may further be used as a return electrode alone or in combination with one or more of the coil electrodes 126, 132 and 134 for shocking or other purposes. Housing 200 further includes a connector (not shown) having a plurality of terminals 201, 202, 204, 206, 208, 212, 214, 216, 218, 221 (shown schematically and, for convenience, the names of the electrodes to which they are connected are shown next to the terminals).

To achieve right atrial sensing, pacing and/or other stimulation, the connector includes at least a right atrial tip terminal ($A_R$ TIP) 202 adapted for connection to the atrial tip electrode 120. A right atrial ring terminal ($A_R$ RING) 201 is also shown, which is adapted for connection to the atrial ring electrode 121. To achieve left chamber sensing, pacing, shocking, and/or autonomic stimulation, the connector includes at least a left ventricular tip terminal ($V_L$ TIP) 204, a left atrial ring terminal ($A_L$ RING) 206, and a left atrial shocking terminal ($A_L$ COIL) 208, which are adapted for connection to the left ventricular tip electrode 122, the left atrial ring electrode 124, and the left atrial coil electrode 126, respectively. Connection to suitable stimulation electrodes is also possible via these and/or other terminals (e.g., via a stimulation terminal S ELEC 221). The terminal S ELEC 221 may optionally be used for sensing.

To support right chamber sensing, pacing, shocking, and/or autonomic nerve stimulation, the connector further includes a right ventricular tip terminal ($V_R$ TIP) 212, a right ventricular ring terminal ($V_R$ RING) 214, a right ventricular shocking terminal (RV COIL) 216, and a superior vena cava shocking terminal (SVC COIL) 218, which are adapted for connection to the right ventricular tip electrode 128, right ventricular ring electrode 130, the RV coil electrode 132, and the SVC coil electrode 134, respectively.

At the core of the stimulation device 100 is a programmable microcontroller 220 that controls the various modes of cardiac or other therapy. As is well known in the art, microcontroller 220 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, microcontroller 220 includes the ability to process or monitor input signals (data or information) as controlled by a program code stored in a designated block of memory. The type of microcontroller is not critical to the described implementations. Rather, any suitable microcontroller 220 may be used that is suitable to carry out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. Nos. 4,712,555 (Thornander) and 4,944,298 (Sholder), all of which are incorporated by reference herein. For a more detailed description of the various timing intervals used within the stimulation device and their inter-relationship, see U.S. Pat. No. 4,788,980 (Mann et al.), also incorporated herein by reference.

FIG. 2 also shows an atrial pulse generator 222 and a ventricular pulse generator 224 that generate pacing stimulation pulses for delivery by the right atrial lead 104, the coronary sinus lead 106, and/or the right ventricular lead 108 via an electrode configuration switch 226. It is understood that in order to provide stimulation therapy in each of the four chambers of the heart (or to autonomic nerves) the atrial and ventricular pulse generators, 222 and 224, may include dedicated, independent pulse generators, multiplexed pulse generators, or shared pulse generators. The pulse generators 222 and 224 are controlled by the microcontroller 220 via appropriate control signals 228 and 230, respectively, to trigger or inhibit the stimulation pulses.

Microcontroller 220 further includes timing control circuitry 232 to control the timing of the stimulation pulses (e.g., pacing rate, atrio-ventricular (AV) delay, interatrial conduction (A-A) delay, or interventricular conduction (V-V) delay, etc.) as well as to keep track of the timing of refractory periods, blanking intervals, noise detection windows, evoked response windows, alert intervals, marker channel timing, etc., which is well known in the art.

Microcontroller 220 further includes an arrhythmia detector 234. The detector 234 can be utilized by the stimulation device 100 for determining desirable times to administer various therapies. The detector 234 may be implemented in hardware as part of the microcontroller 220, or as software/firmware instructions programmed into the device and executed on the microcontroller 220 during certain modes of operation.

Microcontroller 220 further includes a morphology discrimination module 236, a capture detection module 237 and an auto sensing module 238. These modules are optionally used to implement various exemplary recognition algorithms and/or methods presented below. The aforementioned components may be implemented in hardware as part of the microcontroller 220, or as software/firmware instructions programmed into the device and executed on the microcontroller 220 during certain modes of operation. The capture detection module 237, as described herein, may aid in acquisition, analysis, etc., of information relating to IEGMs and, in particular, act to distinguish capture versus non-capture versus fusion.

The electronic configuration switch 226 includes a plurality of switches for connecting the desired electrodes to the appropriate I/O circuits, thereby providing complete electrode programmability. Accordingly, switch 226, in response to a control signal 242 from the microcontroller 220, determines the polarity of the stimulation pulses (e.g., unipolar, bipolar, etc.) by selectively closing the appropriate combination of switches (not shown) as is known in the art.

Atrial sensing circuits 244 and ventricular sensing circuits 246 may also be selectively coupled to the right atrial lead 104, coronary sinus lead 106, and the right ventricular lead 108, through the switch 226 for detecting the presence of cardiac activity in each of the four chambers of the heart. Accordingly, the atrial (ATR. SENSE) and ventricular (VTR. SENSE) sensing circuits, 244 and 246, may include dedicated sense amplifiers, multiplexed amplifiers, or shared amplifiers. Switch 226 determines the "sensing polarity" of the cardiac signal by selectively closing the appropriate switches, as is also known in the art. In this way, the clinician may program the sensing polarity independent of the stimulation polarity. The sensing circuits (e.g., 244 and 246) are optionally capable of obtaining information indicative of tissue capture.

Each sensing circuit 244 and 246 preferably employs one or more low power, precision amplifiers with programmable gain and/or automatic gain control, bandpass filtering, and a threshold detection circuit, as known in the art, to selectively sense the cardiac signal of interest. The automatic gain control enables the device 100 to deal effectively with the difficult problem of sensing the low amplitude signal characteristics of atrial or ventricular fibrillation.

The outputs of the atrial and ventricular sensing circuits 244 and 246 are connected to the microcontroller 220, which, in turn, is able to trigger or inhibit the atrial and ventricular pulse generators 222 and 224, respectively, in a demand fashion in response to the absence or presence of cardiac activity in the appropriate chambers of the heart. Furthermore, as described herein, the microcontroller 220 is also capable of analyzing information output from the sensing circuits 244 and 246 and/or the data acquisition system 252 to determine or detect whether and to what degree tissue capture has occurred and to program a pulse, or pulses, in response to such determinations. The sensing circuits 244 and 246, in turn, receive control signals over signal lines 248 and 250 from the microcontroller 220 for purposes of controlling the gain, threshold, polarization charge removal circuitry (not shown), and the timing of any blocking circuitry (not shown) coupled to the inputs of the sensing circuits, 244 and 246, as is known in the art.

For arrhythmia detection, the device 100 may utilize the atrial and ventricular sensing circuits, 244 and 246, to sense cardiac signals to determine whether a rhythm is physiologic or pathologic. Of course, other sensing circuits may be available depending on need and/or desire. In reference to arrhythmias, as used herein, "sensing" is reserved for the noting of an electrical signal or obtaining data (information), and "detection" is the processing (analysis) of these sensed signals and noting the presence of an arrhythmia or of a precursor or other factor that may indicate a risk of or likelihood of an imminent onset of an arrhythmia.

The exemplary detector module 234, optionally uses timing intervals between sensed events (e.g., P-waves, R-waves, and depolarization signals associated with fibrillation which are sometimes referred to as "F-waves" or "Fib-waves") and to perform one or more comparisons to a predefined rate zone limit (i.e., bradycardia, normal, low rate VT, high rate VT, and fibrillation rate zones) and/or various other characteristics (e.g., sudden onset, stability, physiologic sensors, and morphology, etc.) in order to determine the type of remedial therapy (e.g., anti-arrhythmia, etc.) that is desired or needed (e.g., bradycardia pacing, anti-tachycardia pacing, cardioversion shocks or defibrillation shocks, collectively referred to as "tiered therapy"). Similar rules can be applied to the atrial channel to determine if there is an atrial tachyarrhythmia or atrial fibrillation with appropriate classification and intervention.

Figure 11:
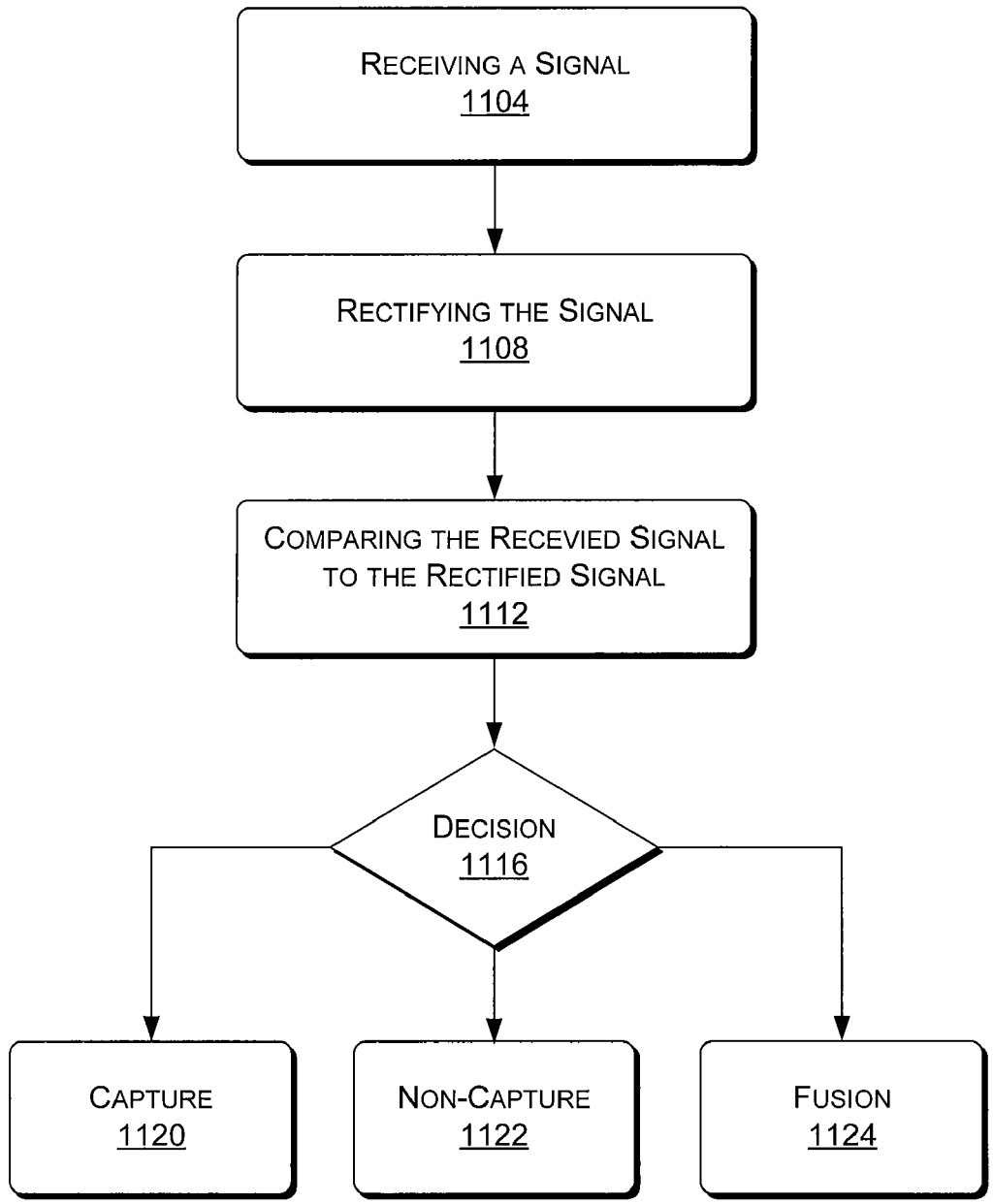
FIG. 11 is a block diagram of an exemplary method for rectifying a signal and deciding whether capture, non-capture or fusion occurred.

Cardiac signals are also applied to inputs of an analog-to-digital (A/D) data acquisition system 252. Additional configurations are shown in FIG. 11 and described further below. The data acquisition system 252 is configured to acquire intracardiac electrogram (IEGM) signals or other action potential signals, convert the raw analog data into a digital signal, and store the digital signals for later processing and/or telemetric transmission to an external device 254. The data acquisition system 252 is coupled to the right atrial lead 104, the coronary sinus lead 106, the right ventricular lead 108 and/or the nerve stimulation lead through the switch 226 to sample cardiac signals across any pair of desired electrodes.

Various exemplary mechanisms for signal acquisition are described herein that optionally include use of one or more analog-to-digital converter. Various exemplary mechanisms allow for adjustment of one or more parameter associated with signal acquisition.

The microcontroller 220 is further coupled to a memory 260 by a suitable data/address bus 262, wherein the programmable operating parameters used by the microcontroller 220 are stored and modified, as required, in order to customize the operation of the stimulation device 100 to suit the needs of a particular patient. Such operating parameters define, for example, pacing pulse amplitude, pulse duration, electrode polarity, rate, sensitivity, automatic features, arrhythmia detection criteria, and the amplitude, waveshape, number of pulses, and vector of each shocking pulse to be delivered to the patient's heart 102 within each respective tier of therapy. One feature of the described embodiments is the ability to sense and store a relatively large amount of data (e.g., from the data acquisition system 252), which data may then be used for subsequent analysis to guide the programming of the device.

Advantageously, the operating parameters of the implantable device 100 may be non-invasively programmed into the memory 260 through a telemetry circuit 264 in telemetric communication via communication link 266 with the external device 254, such as a programmer, transtelephonic transceiver, or a diagnostic system analyzer. The microcontroller 220 activates the telemetry circuit 264 with a control signal 268. The telemetry circuit 264 advantageously allows intracardiac electrograms (IEGM) and other information (e.g., status information relating to the operation of the device 100, etc., as contained in the microcontroller 220 or memory 260) to be sent to the external device 254 through an established communication link 266.

The stimulation device 100 can further include one or more physiologic sensors 270. For example, the device 100 may include a "rate-responsive" sensor that may provide, for example, information to aid in adjustment of pacing stimulation rate according to the exercise state of the patient. However, the one or more physiological sensors 270 may further be used to detect changes in cardiac output (see, e.g., U.S. Pat. No. 6,314,323, entitled "Heart stimulator determining cardiac output, by measuring the systolic pressure, for controlling the stimulation", to Ekwall, issued Nov. 6, 2001, which discusses a pressure sensor adapted to sense pressure in a right ventricle and to generate an electrical pressure signal corresponding to the sensed pressure, an integrator supplied with the pressure signal which integrates the pressure signal between a start time and a stop time to produce an integration result that corresponds to cardiac output), changes in the physiological condition of the heart, or diurnal changes in activity (e.g., detecting sleep and wake states). Accordingly, the microcontroller 220 responds by adjusting the various pacing parameters (such as rate, AV Delay, V-V Delay, etc.) at which the atrial and ventricular pulse generators, 222 and 224, generate stimulation pulses.

While shown as being included within the stimulation device 100, it is to be understood that one or more of the physiologic sensors 270 may also be external to the stimulation device 100, yet still be implanted within or carried by the patient. Examples of physiologic sensors that may be implemented in device 100 include known sensors that, for example, sense respiration rate, pH of blood, ventricular gradient, cardiac output, preload, afterload, contractility, and so forth. Another sensor that may be used is one that detects activity variance, wherein an activity sensor is monitored diurnally to detect the low variance in the measurement corresponding to the sleep state. For a complete description of the activity variance sensor, the reader is directed to U.S. Pat. No. 5,476,483 (Bornzin et. al), issued Dec. 19, 1995, which patent is hereby incorporated by reference.

The one or more physiological sensors 270 optionally include sensors for detecting movement and minute ventilation in the patient. Signals generated by a position sensor, a MV sensor, etc., may be passed to the microcontroller 220 for analysis in determining whether to adjust the pacing rate, etc. The microcontroller 220 may monitor the signals for indications of the patient's position and activity status, such as whether the patient is climbing upstairs or descending downstairs or whether the patient is sitting up after lying down.

The stimulation device 100 additionally includes a battery 276 that provides operating power to all of the circuits shown in FIG. 2. For the stimulation device 100, which employs shocking therapy, the battery 276 is capable of operating at low current drains for long periods of time (e.g., preferably less than 10 μA), and is capable of providing high-current pulses (for capacitor charging) when the patient requires a shock pulse (e.g., preferably, in excess of 2 A, at voltages above 200 V, for periods of 10 seconds or more). The battery 276 also desirably has a predictable discharge characteristic so that elective replacement time can be detected.

The stimulation device 100 can further include magnet detection circuitry (not shown), coupled to the microcontroller 220, to detect when a magnet is placed over the stimulation device 100. A magnet may be used by a clinician to perform various test functions of the stimulation device 100 and/or to signal the microcontroller 220 that the external programmer 254 is in place to receive or transmit data to the microcontroller 220 through the telemetry circuits 264.

The stimulation device 100 further includes an impedance measuring circuit 278 that is enabled by the microcontroller 220 via a control signal 280. The known uses for an impedance measuring circuit 278 include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring stroke volume; and detecting the opening of heart valves, etc. The impedance measuring circuit 278 is advantageously coupled to the switch 226 so that any desired electrode may be used.

In the case where the stimulation device 100 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 220 further controls a shocking circuit 282 by way of a control signal 284. The shocking circuit 282 generates shocking pulses of low (e.g., up to 0.5 J), moderate (e.g., 0.5 J to 10 J), or high energy (e.g., 11 J to 40 J), as controlled by the microcontroller 220. Such shocking pulses are applied to the patient's heart 102 through at least two shocking electrodes, and as shown in this embodiment, selected from the left atrial coil electrode 126, the RV coil electrode 132, and/or the SVC coil electrode 134. As noted above, the housing 200 may act as an active electrode in combination with the RV electrode 132, or as part of a split electrical vector using the SVC coil electrode 134 or the left atrial coil electrode 126 (i.e., using the RV electrode as a common electrode).

Cardioversion level shocks are generally considered to be of low to moderate energy level (so as to minimize pain felt by the patient), and/or synchronized with an R-wave and/or pertaining to the treatment of tachycardia. Defibrillation shocks are generally of moderate to high energy level (e.g., corresponding to thresholds in the range of approximately 5 J to 40 J), delivered asynchronously (since R-waves may be too disorganized), and pertaining exclusively to the treatment of fibrillation. Accordingly, the microcontroller 220 is capable of controlling the synchronous or asynchronous delivery of the shocking pulses.

In a normal heart, cells of the sinoatrial node (SAN) spontaneously depolarize and thereby initiate an action potential. This action potential propagates rapidly through the atria (which contract), slowly through the atrioventricular node (AVN) and then to the ventricles, which causes ventricular contraction. Thus, in a normal heart, ventricular rhythm relies on intrinsic or native atrial action potentials and conduction of such action potentials through the AVN.

An electrocardiogram (ECG) of normal heart activity (e.g., polarization, depolarization, etc.) typically shows atrial depolarization as a "P wave", ventricular depolarization as an "R wave", or QRS complex, and repolarization as a "T wave".

Figure 3:
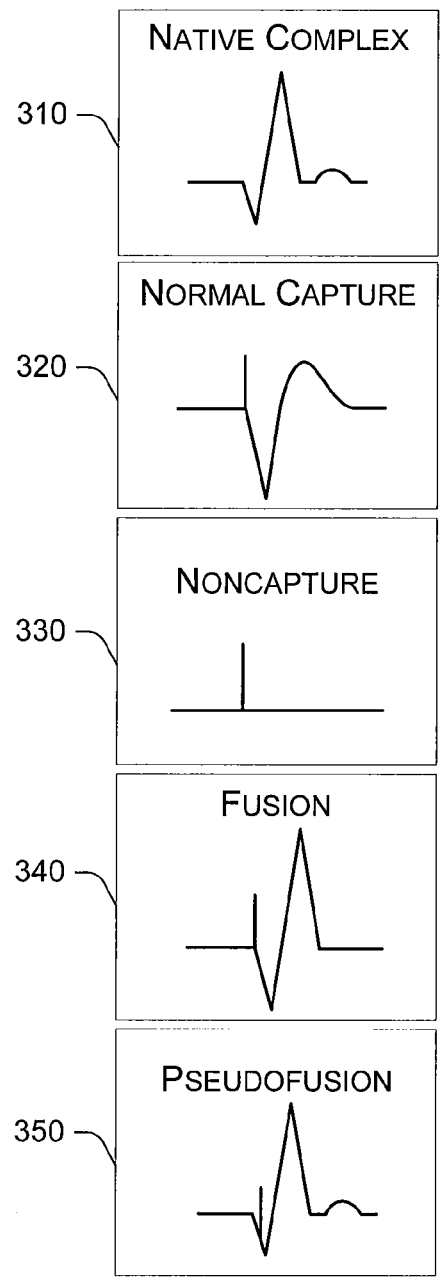
FIG. 3 is a series of plots of exemplary cardiac waveforms.

Referring to FIG. 3, various exemplary ventricular waveforms 300 are shown. As discussed herein, a ventricular waveform caused by a ventricular stimulus is generally referred to as an evoked response while a ventricular waveform caused by a native stimulus (e.g., conducted SAN action) is generally referred to as an R wave or native QRS complex. The exemplary waveforms 300 include a native waveform 310 (e.g., per an ECG), which exhibits a distinct QRS complex and a distinct T wave. A paced ventricular waveform 320 that results in capture (i.e., an evoked response) differs from the native waveform 310. For example, a typical evoked response obscures at least some repolarization; hence, the paced ventricular waveform 320 may lack a distinct T wave. If the ventricles are refractory or if the stimulus energy is insufficient, then a non-capture waveform results 330. The particular non-capture waveform 330 corresponds to a scenario lacking native or intrinsic activity; the stylized waveform exhibits a stimulus artifact only. Of course, intracardiacelectrograms (IEGMs) acquired with use of a blanking interval may not exhibit such a stimulus artifact.

Fusion is typically characterized by a wave complex formed by depolarization of the myocardium initiated by two different foci, commonly a non-native stimulus as from a pacemaker or ICD and a native stimulus. As shown in FIG. 3, a fusion waveform 340 includes characteristics of a native waveform and a paced ventricular waveform. In particular, the waveform 340 includes depolarization due to an administered stimulus.

In contrast to fusion, pseudofusion is typically characterized by a wave complex formed by depolarization of the myocardium initiated by a native stimulus; however, a non-native stimulus, that does not significantly contribute to depolarization, is present that distorts the wave complex. The exemplary waveforms 300 include a pseudofusion waveform 350, which exhibits a native waveform and a stimulus artifact wherein the stimulus does not significantly contribute to depolarization. As described herein, a waveform indicative of fusion may be referred to as a "fusion beat" and a waveform indicative of pseudofusion may be referred to as a "pseudofusion beat".

Fusion and Pseudofusion in Pacing Therapy

In traditional pacing systems, fusion and pseudofusion beats are typically inconsequential without adverse effects on a patient; although, such beats may result in some confusion on the part of the medical staff caring for the patient. In more advanced pacing systems, however, fusion and/or pseudofusion beats may seriously interfere with objectives of some algorithms and therapies. For example, an algorithm that detects capture may misinterpret a fusion waveform or a pseudofusion waveform as a loss of capture and, in response, deliver a back-up stimulus or commence a capture threshold search algorithm.

Regarding delivery of a back-up stimulus, such action is unwarranted because native activity is present (i.e., native activity always accompanies fusion). Further, delivery of an unwarranted back-up stimulus needlessly diminishes an implantable device's limited power supply. Regarding commencement of a capture threshold search algorithm, such action is unwarranted because fusion is primarily a timing issue and not a stimulation energy issue.

A particular threshold search uses the AUTOCAPTURE™ algorithm (St. Jude Medical, Cardiac Rhythm Management Division, Sylmar, Calif.) to automatically adjust output and/or assess capture threshold. The AUTOCAPTURE™ algorithm runs a capture threshold assessment test once every eight hours. To perform this test, the paced and sensed AV delays are temporarily shortened to about 50 ms and to about 25 ms, respectively. The AUTOCAPTURE™ algorithm generally uses a bottom-up approach (also referred to as an "up threshold") and a back-up pulse for safety when an output pulse does not result in capture. With respect to use of a back-up pulse, an output pulse of about 4.5 volts is typically sufficient to achieve capture.

In clinical follow-up, a care provider may perform a threshold test to determine if the algorithm for capture is working properly and for further assessment. In systems that use the AUTOCAPTURE™ algorithm, a follow-up clinical test includes automatically and temporarily setting PV delay and AV delay times to about 25 ms and about 50 ms, respectively, which acts to minimize risk of fusion. As already discussed, fusion may compromise measurement of an evoked response (ER) signal, especially ER signal amplitude.

The follow-up tests typically work top down. If loss of capture occurs, a first output adjustment step typically sets a high output and then decreases output by about 0.25 volts until loss of capture occurs (also referred to as a "down threshold"). At this point, output is increased by a lesser amount (e.g., about 0.125 volts) until capture occurs. Once capture occurs, a working or functional margin of about 0.25 volts is added to the capture threshold output value. Hence, the final output value used is the capture threshold plus a working margin. Systems that use a fixed output use a safety margin ratio instead of an absolute added amount. The safety margin is a multiple of the measured capture threshold, commonly 2:1 or 100% to allow for fluctuations in the capture threshold between detailed evaluations at the time of office visits.

As discussed herein, in instances where a detected loss of capture is actually fusion, then there is no need to adjust stimulation threshold for the particular stimulation site. Further, there is typically no need to alter atrioventricular delay. Yet further, where an atrioventricular delay has been optimized to improve cardiac performance, any adjustment to this parameter can be expected to affect cardiac performance adversely.

Another pacing therapy that can benefit from recognition of fusion and pseudofusion is dual chamber pacing (e.g., an atrial chamber and a ventricular chamber) for management of hypertrophic obstructive cardiomyopathy (HOCM). HOCM pacing therapy typically relies on full ventricular capture, i.e., ventricular stimulus and ventricular capture prior to arrival of a native stimulus or a paced atrial stimulus. Thus, HOCM pacing algorithms often use a short AV interval to ensure delivery of the ventricular stimulus prior to arrival of any native or paced atrial stimuli. For example, an algorithm may sense an atrial event, commence an AV interval and then deliver a ventricular stimulus upon expiration of the AV interval. However, many HOCM patients have short baseline P wave to R wave intervals; thus, to avoid fusion or pseudofusion an algorithm may implement a very short AV interval, indeed, possibly too short for effective atrial contraction and ventricular filling. In addition, some algorithms for management of HOCM also account for P wave to R wave interval shortening associated with an increased intrinsic heart rate. Overall, in HOCM patients having adequate AV nodal conduction, if the AV interval is too long, the risk of fusion and pseudofusion increases and hence, so does the risk of inadequate ventricular action. Thus, fusion and/or pseudofusion may be counterproductive and compromise intended hemodynamic benefits. Consequently, exemplary recognition algorithms presented herein can improve HOCM therapy.

Cardiac resynchronization therapy (CRT) can also benefit from an ability to distinguish capture from loss of capture or fusion. Again, when fusion is detected as loss of capture, then an unnecessary threshold search may occur, for example, using a capture threshold search algorithm (e.g., AUTOCAPTURE™, St. Jude Medical, Inc., Sylmar, Calif.). Unnecessary threshold searches can waste energy, interrupt or alter therapy and, in some instances, affect patient comfort.

CRT aims to improve cardiac function through judicious timing of ventricular contractions. Often, CRT includes pacing the left ventricle and the right ventricle in a manner that optimizes cardiac output or one or more other cardiac functions. For example, for a given AV for the right ventricle (i.e., $AV_{RV}$), a CRT algorithm can set a left ventricular AV (i.e., $AV_{LV}$) that aims to improve synchrony between left and right ventricular contractions. Of course, $PV_{RV}$ or $PV_{LV}$ may be used and, depending on the cardiac condition, a native ventricular event may be used (e.g., AR or PR) in a CRT algorithm. Regardless of the manner in which ventricular contractions are initiated, an important CRT parameter is the interventricular delay (VV).

As already mentioned, a capture detection algorithm can alter an atrioventricular delay and thereby affect VV and delivery of CRT. Further, in CRT that involves left ventricular and right ventricular stimulation, loss of capture may occur in either or both ventricles. Consequently, such bi-ventricular stimulation CRT can experience a higher incidence of fusion and a higher incidence of actual loss of capture when compared to a therapy that involves pacing a single ventricle. Thus, an ability to maintain the therapy during a threshold search (and hence distinguish capture from fusion from loss of capture, and not changing the timings to reduce the likelihood of fusion) becomes more desirable and beneficial for CRT patients.

Various exemplary methods, devices, systems, etc., described herein can discriminate fusion, capture and loss of capture and, in turn, allow for more consistent delivery of CRT, mainly by avoiding unnecessary threshold searches.

While fusion and pseudofusion avoidance can improve some pacing therapies, other pacing therapies can benefit from algorithms that help promote fusion. For example, some multisite pacing therapies for dilated cardiomyopathy and congestive heart failure actually rely on fusion because the resulting ventricular activation sequence provides the best hemodynamic results. Therefore, various exemplary fusion and/or pseudofusion recognition algorithms can enhance performance of particular pacing therapies.

In general, verification of capture can be achieved more readily than verification of non-capture or loss of capture because fusion can interfere with an evoked response waveform (see, e.g., the waveform 340 of FIG. 3). In particular, fusion can diminish the amplitude of an evoked response waveform and, in turn, be detected as non-capture.

Figure 4:
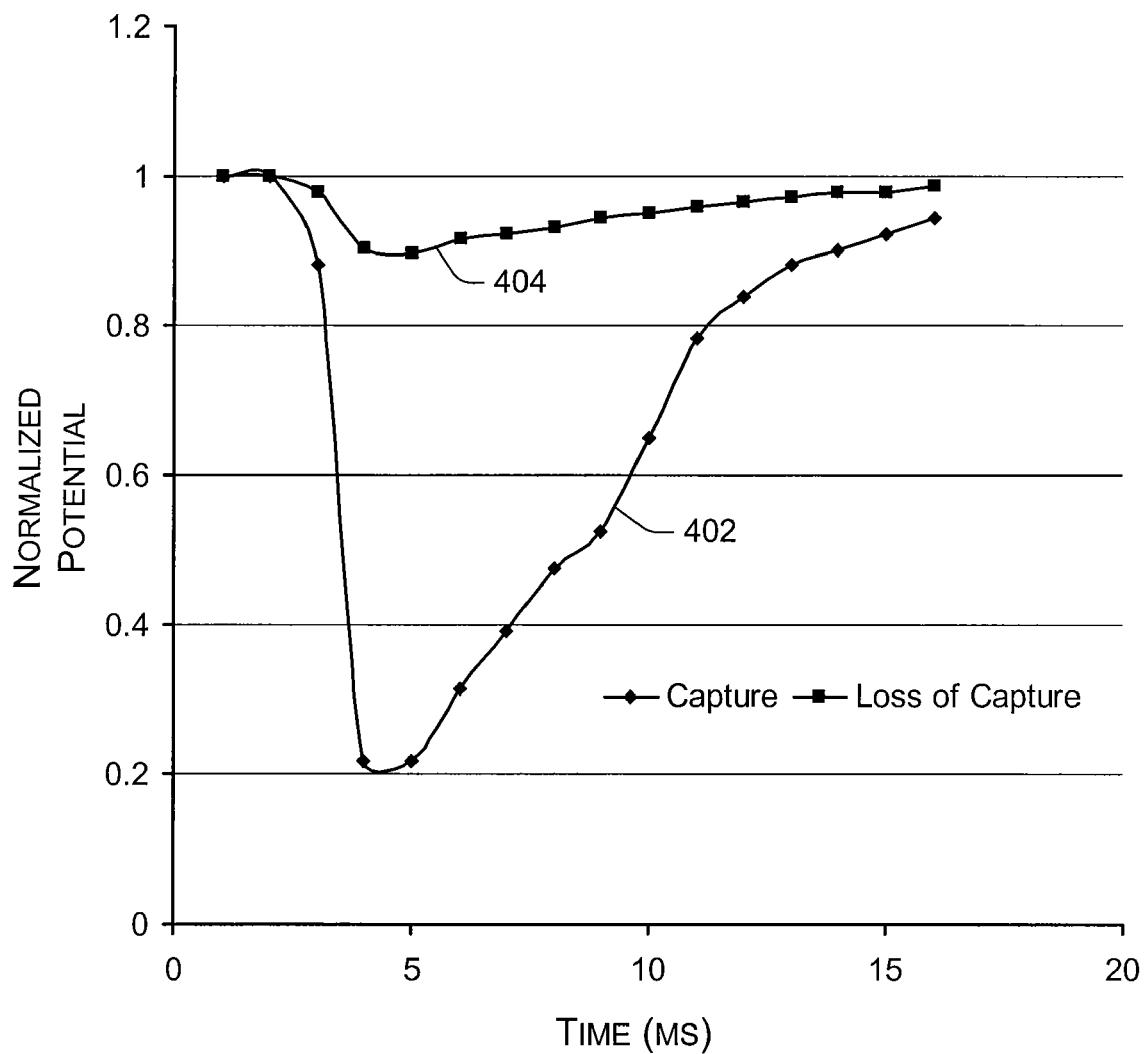
FIG. 4 is a plot of normalized potential versus time for a capture scenario and a non-capture or loss of capture scenario.

An example of a sensed capture event and non-capture or loss of capture event is shown in FIG. 4. FIG. 4 shows an exemplary plot 400 of normalized potential versus time for a stimulus that resulted in an evoked response (402, diamond markers) and for a stimulus that did not result in an evoked response (404, square markers). A stimulus that results in an evoked response is classified "capture" while a stimulus that does not result in an evoked response is classified as "non-capture". When non-capture follows capture, then the response may be classified as loss of capture. Such plots of potential versus time, when acquired by an implanted device, are typically referred to as intracardiac electrograms or IEGMs. Some conventional implantable cardiac therapy devices are capable of acquiring, analyzing and even storing IEGMs.

The potentials over time for the capture and the non-capture scenarios of the plot 400 include contributions from cardiac activity and other activity. Cardiac activity includes depolarization of cardiac tissue and repolarization of cardiac tissue. Such activity may exist even in absence of "capture" as localized depolarization near an electrode may occur following a sub-threshold stimulus that is insufficient to cause global depolarization, i.e., insufficient to cause capture. Other activity includes artifacts such as electrode polarization, which is present to some degree whenever a potential is applied across two electrodes (e.g., whether unipolar, bipolar, etc.). As a consequence, various detection algorithms rely on one or more thresholds in amplitude, potential-time integral, amplitude-time derivative, etc., to better distinguish capture from non-capture.

Where a detection algorithm relies on amplitude, fusion may decrease amplitude to a level that falls below an amplitude threshold; where a detection algorithm relies on a potential-time integral, fusion may decrease the integral to a level that falls below an integral threshold; and where a detection algorithm relies on an amplitude-time derivative, fusion may decrease the derivative to a level that falls below a derivative (e.g., slope) threshold. Of course, other techniques exist for analyzing a post-stimulus IEGM. In general, however, most analysis techniques do not accurately and reliably distinguish capture, non-capture and fusion.

Figure 5:
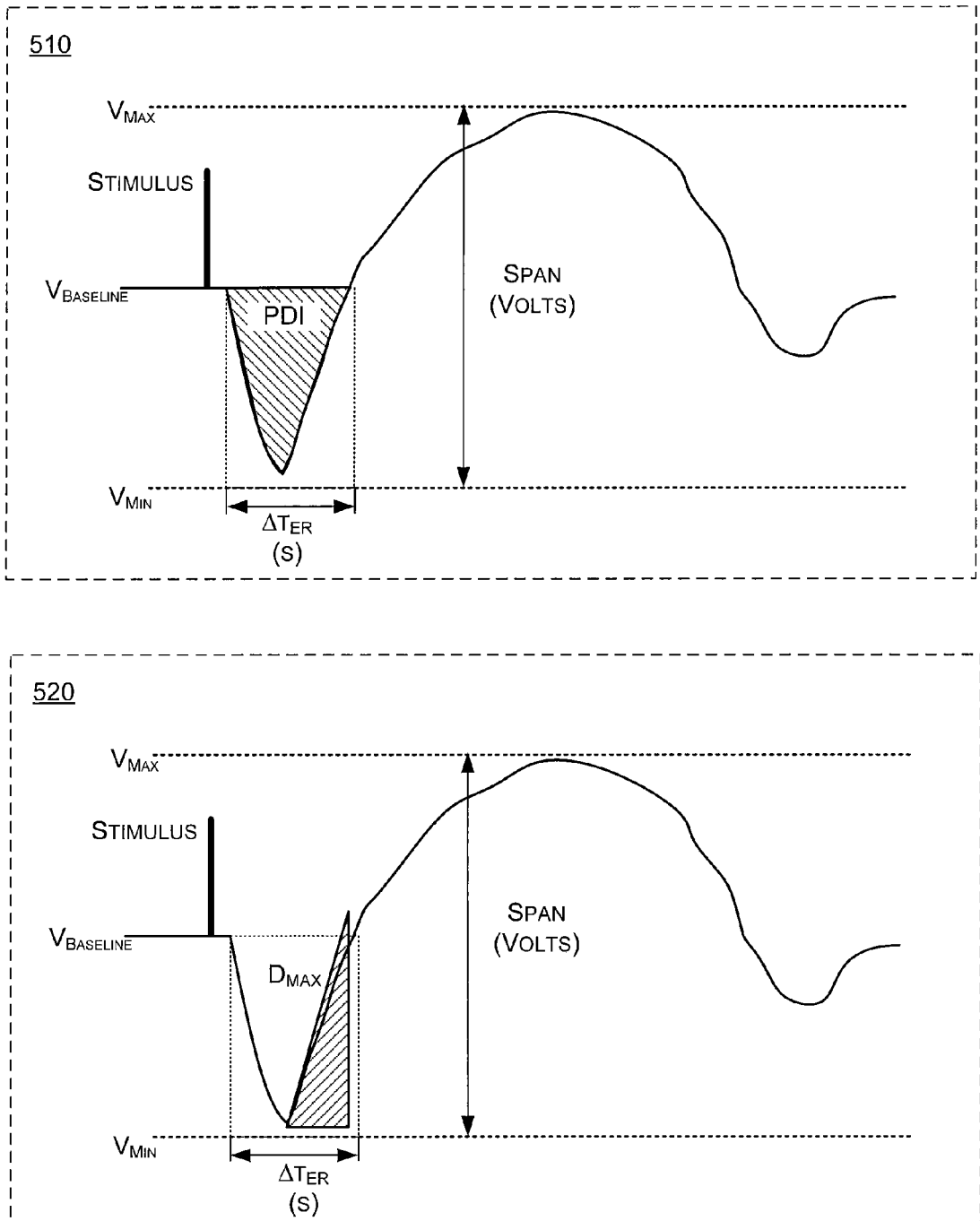
FIG. 5 is a plot illustrating a post-depolarization integral (PDI) analysis technique and a plot illustrating of a maximum derivative ($D_{Max}$) analysis technique.

FIG. 5 shows two plots 510, 520 of an IEGM and an integral analysis technique and a derivative analysis technique, respectively. The potential signal in both instances corresponds to an evoked response, responsive to a cardiac stimulus. As shown in the plots 510, 520, both of the IEGMs decrease from a baseline to a minimum as a result of tissue depolarization.

Both of the IEGM plots 510, 520 include various parameters associated with data acquisition and/or data analysis. For example, a span in volts defined by a maximum voltage ($V_{Max}$) and a minimum voltage ($V_{Min}$) and duration of a sampling window or period in seconds ($\Delta T_{ER}$). Data acquisition may also rely on an offset voltage ($V_{Offset}$). In general, data acquisition occurs after a delay or void window with duration in seconds ($\Delta t_V$). The void window may be due to any of a variety of actions that prevent a signal from being sampled or disregard sampled information (e.g., blanking, blocking, recharge, device refractory, etc.). For example, a device may include a void window or period to minimize interference from a stimulus or after polarization. In the latter instance, some devices may apply a counter potential to minimize after polarization prior to sampling of a signal (e.g., recharge). A device may use a device refractory window wherein sampled information is ignored, not analyzed, not stored, etc. In general, a sampling window may commence after all blanking, device refractory windows, etc.

A blanking or a blocking window may aim to ensure that ringing does not occur in a sense amplifier. This may be accomplished via software and/or hardware. For example, hardware blocking may include switching to electrically disconnect a lead conductor from a circuit during delivery of a cardiac stimulus and hardware blanking may include shorting a lead conductor or amplifier input during delivery of a cardiac stimulus while software blanking may ignore output of a sensing amplifier. A recharge window may immediately follow a pacing stimulus and include reversing current flow across the stimulus electrodes to reduce electrode polarization.

Referring again to the plot 510, integration analysis may include determining a depolarization integral (PDI), which may, sometimes, be referred to as a post-depolarization integral or a paced-depolarization integral. A PDI may be determined by summing acquired potential values for a given sampling window (e.g., $\Delta T_{ER}$). Typically, a sampling duration and a sampling period or frequency allow for determination of a PDI value in units of potential and time. While an integral is shown, other mathematical techniques may be applied to extract information from a depolarization signal. For example, derivative versus time, amplitude versus time, etc., may yield valuable information.

The plot 520 shows a derivative analysis wherein a maximum derivative of potential with respect to time ($D_{Max}$) occurs during a rise from the minimum potential to the baseline potential. In various human models, the maximum derivative typically occurs in range of about 12 ms to about 35 ms after the delivery of a cardiac stimulus. While the maximum derivative occurs during a rise from the minimum to the baseline potential, the time window or increment for calculating the maximum derivative is usually short, on the order of two or more samples at a given sampling rate (e.g., around 2 ms for a sampling rate of about 1 ms). Thus, the shaded region for $D_{Max}$ in the plot 520 represents $D_{Max}$ with respect to about ½ $\Delta T_{ER}$.

Acquisition of data to determine the maximum derivative occurs during a sampling window, $\Delta T_{ER}$. In the plots 510, 520 the sampling window commences after a void duration that follows the stimulus (e.g., $\Delta T_{Void}$, not labeled). In some exemplary methods, devices, systems, etc., described herein the void duration may be reduced and the sampling window commenced.

As fusion can interfere with a post-stimulation IEGM, the PDI for a fusion beat may be significantly less than the PDI for an evoked response and the $D_{Max}$ for a fusion beat may be significantly less than the $D_{Max}$ for an evoked response. For example, consider the two waveforms 402, 404 of FIG. 4. A fusion beat waveform may mimic the waveform 404 or have another waveform that does not exhibit the features of the waveform 402. Where the fusion beat waveform differs substantially from the waveform 402, the PDI and $D_{Max}$ will differ as well, typically being smaller than the PDI and $D_{Max}$ of the waveform 402.

Various exemplary techniques described herein use explicitly or implicitly one or more representations of a post-stimulation IEGM signal. For example, consider the rectified representation of a post-stimulation IEGM signal of FIG. 6 and FIG. 7.

Figure 6:
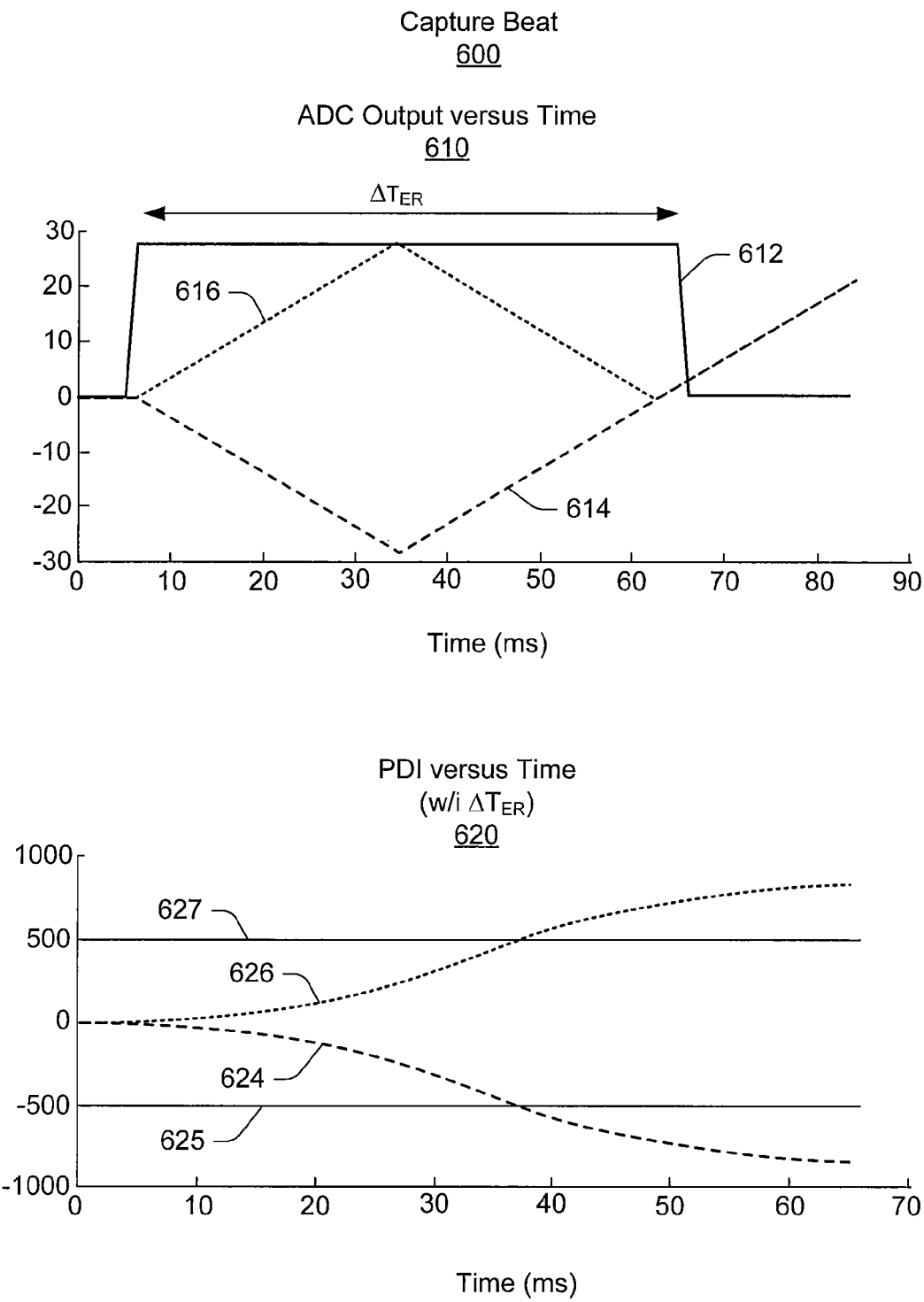
FIG. 6 is a plot of ADC output versus time and a plot of PDI versus time for a capture beat scenario.

FIG. 6 shows a capture beat scenario 600 that includes rectification of a post-stimulation IEGM signal 610 and analysis of the rectified signal 620. The rectification procedure 610 is described with respect to a plot of analog-to-digital converter counts (ADC) versus time in ms (approximately 1024 Hz samples) that includes an acquisition or analysis window $\Delta T_{ER}$ 612, an acquired signal 614 and a rectified signal 616. In this example, the window has a duration of about 60 ms and as described with respect to the plot 620, the PDI values cross the thresholds at around 40 ms, hence for the given signal, the acquisition or analysis window is equal to or greater than about 40 ms. An exemplary procedure may set or adjust the window $\Delta T_{ER}$ 612 based on such information.

The exemplary rectification procedure 610 may rectify a digitized signal or an analog signal. As shown, the rectification results in a signal or values at or above a baseline (e.g., about 0 counts in the example). Further, while not explicitly shown in FIG. 6, an operation such as a subtraction or addition of a rectified and a non-rectified signal may occur. In either instance, the procedure 610 uses a representation of the non-rectified signal (e.g., explicitly or implicitly).

For the capture beat scenario 600, the rectified signal 616 and the non-rectified signal 614 differ significantly during the acquisition or analysis window 612. To take advantage of this difference, the exemplary analysis 620 integrates both the rectified signal 616 and the non-rectified signal 614 and compares the rectified signal integral 626 to a rectified signal integral threshold 627 and compares the non-rectified signal integral 624 to a non-rectified signal integral threshold 625. The thresholds 625, 627 are typically adjusted or set based on acquisition, analysis or other information to indicate that when the rectified signal integral 626 exceeds the rectified signal integral threshold 627 (e.g., rises above the threshold 627) and when the non-rectified signal integral 624 exceeds a non-rectified signal integral threshold 625 (e.g., falls below the threshold 625), capture is verified.

Figure 7:
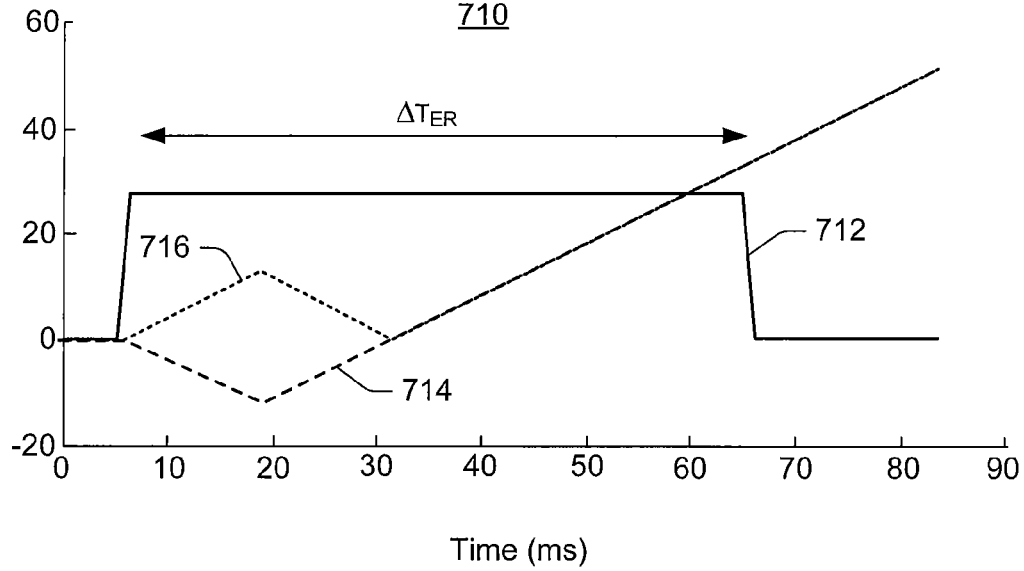
FIG. 7 is a plot of ADC output versus time and a plot of PDI versus time for a fusion beat scenario.
Figure 7:
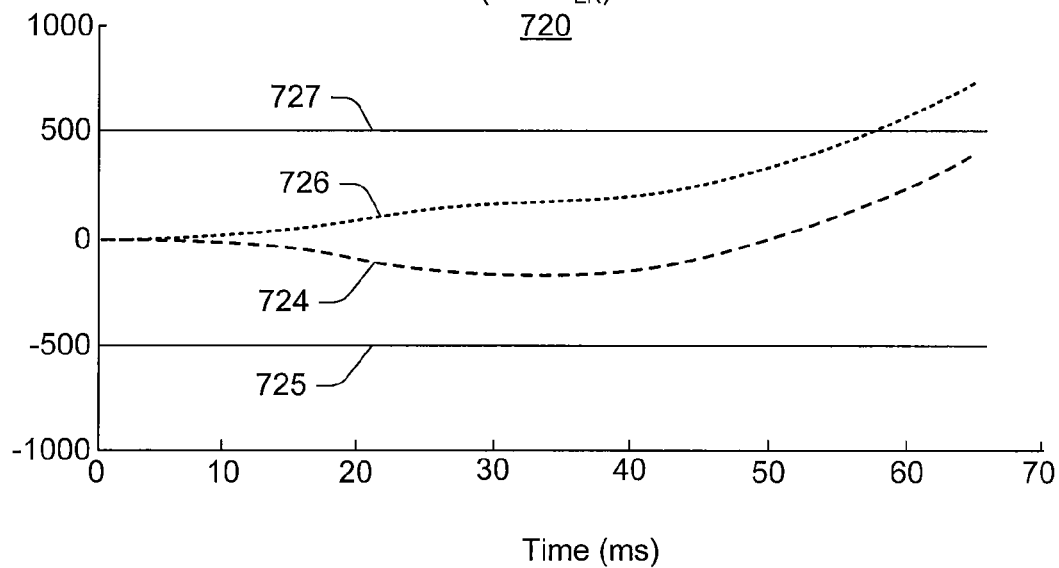

FIG. 7 shows a fusion beat scenario 700 that includes rectification of a post-stimulation IEGM signal 710 and analysis of the rectified signal 720, for example, as explained with respect to FIG. 6. While not explicitly shown in FIG. 7, an operation such as a subtraction or addition of a rectified and a non-rectified signal may occur. In either instance, the procedure 710 uses a representation of the non-rectified signal (e.g., explicitly or implicitly).

For the fusion beat scenario 700, the rectified signal 716 and the non-rectified signal 714 do not differ as significantly during the acquisition or analysis window 712 as in the capture beat scenario 600. Consequently, the exemplary integration analysis 720, which integrates both the rectified signal 716 and the non-rectified signal 714, results in the rectified signal integral 726 exceeding the rectified signal integral threshold 727 (e.g., rises above the threshold 727) and the non-rectified signal integral 724 not exceeding the non-rectified signal integral threshold 725. Thus, the result of the fusion beat scenario 700 differs from the result of capture beat scenario 600.

Figure 8:
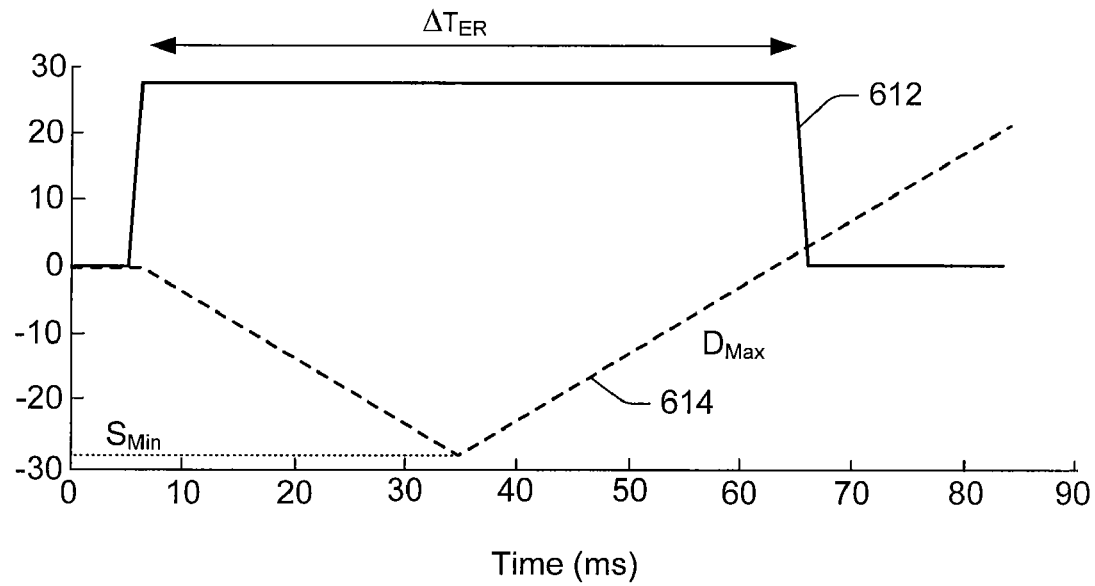
FIG. 8 is a plot of ADC output versus time for a capture beat scenario and a plot of ADC output versus time for a fusion beat scenario.
Figure 8:
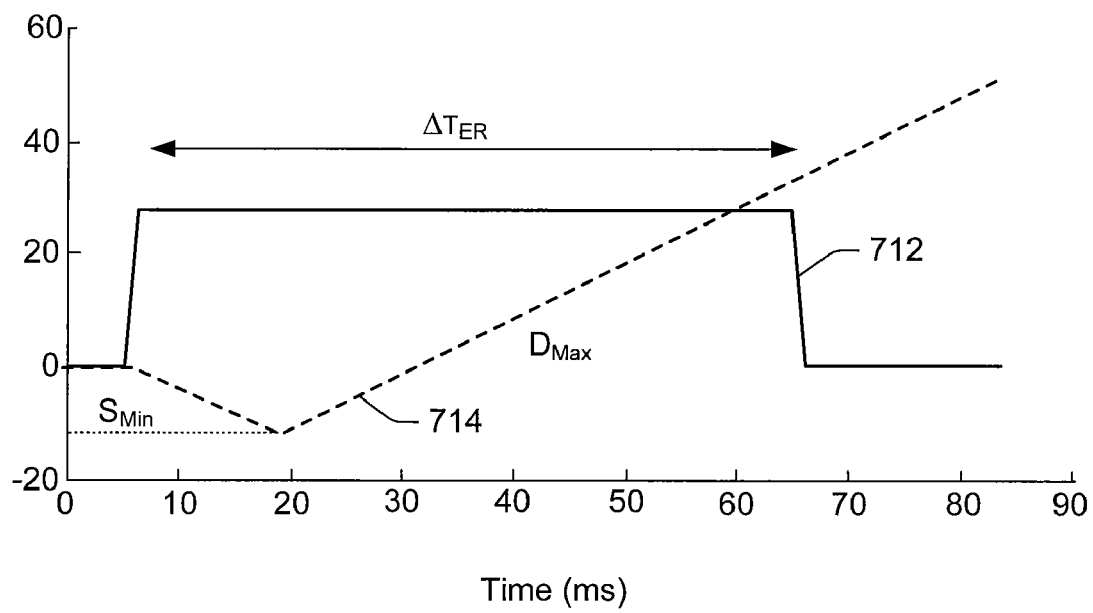

FIG. 8 shows additional information 800 that may be used in conjunction with information such as the rectified signal information to distinguish capture, non-capture and fusion. The additional information 800 includes the non-rectified signal 614 of the capture beat scenario 600 and the non-rectified signal 714 of the fusion beat scenario 700. Also indicated in these stylized hypothetical signals are a minimum signal amplitude $S_{Min}$ (e.g., in ADC counts) and a maximum derivative of signal amplitude with respect to time $D_{Max}$ (e.g., for two or more samples, usually on a time scale that is less than $\Delta T_{ER}$. A comparison indicates that the non-rectified signal 614 of the capture beat has a lesser $S_{Min}$ than the non-rectified signal 714 of the fusion beat and that the non-rectified signal 614 of the capture beat has a slightly greater $D_{Max}$ than the non-rectified signal 714 of the fusion beat. Depending on a $D_{Max}$ threshold or criteria, $D_{Max}$ may not be capable of reliably distinguishing capture from fusion. However, where non-capture occurs, $D_{Max}$ is typically much less than $D_{Max}$ of capture and fusion. Of course, where rectified signals are available, similar information may be gleaned from such signals.

The information presented in FIG. 8 demonstrates that one or more other factors may be used in distinguishing capture, non-capture and fusion. FIG. 9 shows two exemplary tables 910, 920 for deciding whether capture, loss of capture or fusion occurred based on IEGM information. In particular, the table 910 relies on a rectified PDI and a non-rectified PDI to decide whether capture, loss of capture or fusion occurred. In the table 910, the non-rectified PDI corresponds to an integral below a baseline value and the rectified PDI corresponds to an integral above a baseline value. For example, if the baseline were set to zero, then the non-rectified PDI would be negative and the rectified PDI would be positive. In contrast, the table 920 does not rely on a rectified PDI but rather a non-rectified PDI and a $D_{Max}$.

As described for the capture beat scenario 600 of FIG. 6 and the fusion beat scenario 700 of FIG. 7, a threshold exists for the non-rectified PDI and another threshold exists for the rectified PDI. As shown in various examples, the non-rectified PDI threshold is below the baseline and the rectified PDI threshold is above the baseline. Of course, in other examples, these could be reversed (e.g., due to reversed polarity of IEGM, etc.). Where the table 910 indicates that a PDI is greater than a respective threshold, then, whether the PDI is negative or positive, it has exceeded a negative or a positive value, respectively.

According to the table 910, three possible and distinct states exist:

(1) Capture where the rectified PDI exceeds the rectified PDI threshold and where the non-rectified PDI exceeds the non-rectified PDI threshold (see, e.g., the analysis 620 of FIG. 6);

(2) Fusion where the rectified PDI exceeds the rectified PDI threshold and where the non-rectified PDI does not exceed the non-rectified PDI threshold (see, e.g., the analysis 720 of FIG. 7); and (3) Non-capture where the rectified PDI does not exceed the rectified PDI threshold and where the non-rectified PDI does not exceed the non-rectified PDI threshold.

The exemplary table 920 relies on a non-rectified PDI and $D_{Max}$. According to the table 920, three possible and distinct states exist:

(1) Capture where the $D_{Max}$ exceeds a $D_{Max}$ threshold and where the non-rectified PDI exceeds the non-rectified PDI threshold (see, e.g., the analysis 620 of FIG. 6 and the $D_{Max}$ of the IEGM 614 of FIG. 8);

(2) Fusion where the $D_{Max}$ does not exceed a $D_{Max}$ threshold and where the non-rectified PDI does not exceed the non-rectified PDI threshold (see, e.g., the analysis 720 of FIG. 7 and the $D_{Max}$ of the IEGM 714 of FIG. 8); and (3) Non-capture where the non-rectified PDI does not exceed the non-rectified PDI threshold and where $D_{Max}$ does not exceed a $D_{Max}$ threshold.

Figure 10:
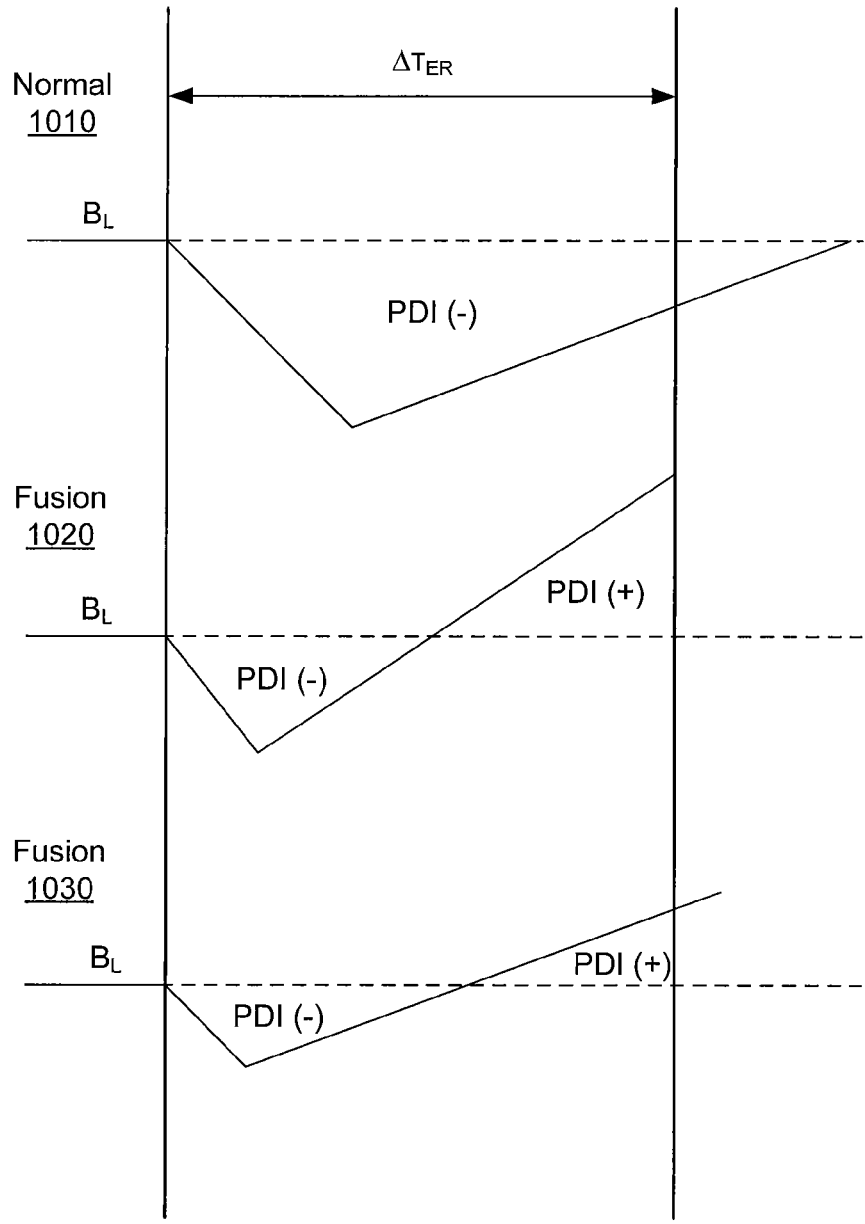
FIG. 10 is a series of plots for an exemplary analysis that uses one or more PDIs to decide if capture, non-capture or fusion occurred following delivery of stimulation energy to the heart.

An exemplary analysis optionally relies on a PDI above a baseline and a PDI below a baseline for a given IEGM, for example, within an evoked response acquisition or analysis window. FIG. 10 shows various exemplary analyses 1000 that include a normal capture beat 1010, a fusion beat 1020 and another fusion beat 1030. The exemplary analyses 1000 may rely on setting an appropriate time for $\Delta T_{ER}$.

The normal capture beat 1010 has a PDI that is "negative" (i.e., below a baseline $B_L$). Further, the window parameter $\Delta T_{ER}$ is set such that the IEGM potential does not rise above the baseline $B_L$ during the window. Consequently, the PDI for a normal capture beat 1010 is negative.

The first fusion beat 1020 has a PDI that is negative (i.e., below a baseline $B_L$) and positive (i.e., above a baseline $B_L$) and the second fusion beat 1030 has a PDI that is negative (i.e., below a baseline $B_L$) and positive (i.e., above a baseline $B_L$). Thus, an exemplary method may rely on a PDI above baseline and a PDI below baseline to decide whether capture of fusion has occurred. One or more thresholds or ratios may be set to further distinguish fusion and non-capture. For example, a positive to negative PDI ratio or a positive capture PDI to positive PDI ratio, etc. As already mentioned, polarity may be reversed or a signal or counts reversed for an analog-to-digital converter, in such circumstances, the comparisons (or thresholds or ratios) may be properly adjusted.

In general, the acquisition or analysis window is covers a range of about 25 ms post-stimulation to about 75 ms post-stimulation (e.g., duration of about 50 ms). The lower end of the range typically depends on blanking, blocking, recharge, etc., associated with the delivery of the stimulation. Where an active charge recovery technique is available, this lower end may commence within a millisecond or a couple of milliseconds after delivery of the stimulation. The upper end of the range may extend beyond 75 ms, for example, about 100 ms may be used. However, the depolarization phase of the evoked response is usually over by 100 ms.

FIG. 2 shows circuitry that may be used to implement various exemplary methods described herein. For example, the programmable microcontroller 220, the capture detection module 237, the switch 226 and the analog-to-digital converter 252 of FIG. 2 may be used. Some examples may use other circuitry or additional circuitry. For example, an additional analog-to-digital converter (A/D) may be used, one or more hardware integrators, etc.

An exemplary method may integrate a normal signal from an A/D to provide a normal (non-rectified) integral value and integrate a rectified signal from an A/D to provide a rectified integral value and then compare the two integral values to determine whether capture, fusion or non-capture occurred. Table 910 of FIG. 9 shows how such a determination can be made based on a rectified PDI and a non-rectified PDI when each is compared to a threshold value. This alternative method may omit use of a threshold and compare the integrals directly. Further, additional information (e.g., $D_{Max}$) may be used to confirm or increase certainty of a determination.

An exemplary method may rely on subtraction of a rectified signal (or integral thereof) from a non-rectified signal (or integral thereof), or vice versa, as a type of comparison. An exemplary method may use a non-rectified signal (or characteristic thereof) for purposes of capture detection and then use a rectified signal (or characteristic thereof) to decide whether fusion or actual capture occurred. In such a method, signal characteristics may include integrals, derivatives, amplitudes, etc. In such a method, the decision as to whether fusion or actual capture occurred may rely on comparing the rectified signal (or characteristic thereof) to a threshold or to the non-rectified signal (or characteristic thereof).

The device 100 of FIG. 2, or other exemplary device, may include a circuit to process an analog signal from the switch 226 and to provide the processed analog signal to the A/D 252. Such a circuit may be controlled by the microcontroller 220. Such a circuit may rectify an analog signal on a continuous or periodic basis, for example, the circuit may rectify according to a clock signal such that every other sample produced by the A/D 252 corresponds to a rectified signal. Thus, in this example, the A/D 252 outputs a mix of rectified and non-rectified values that can be appropriately integrated and analyzed by the capture detection module 237.

FIG. 11 shows an exemplary method 1100 for rectifying a signal and deciding whether capture, non-capture or fusion occurred. A reception block 1104 receives a signal of cardiac electrical activity after delivery of electrical energy to the heart. A rectification block 1108 rectifies the received signal to produce a rectified signal. A comparison block 1112 compares the received signal (i.e., unrectified) to the rectified signal. For example, the plot 610 and the plot 620 of FIG. 6 show an unrectified signal 614, 624 compared to a rectified signal 616, 626. A decision block 1116 then decides, based at least in part on the comparison, whether the delivered electrical energy resulted in capture 1120, non-capture 1122 or fusion 1124. For example, the decision block 1116 may rely on a decision table (e.g., table 910, table 920) to make such a decision. Following a decision, appropriate action may follow (e.g., adjusting a timing parameter, increasing energy, etc.).

CONCLUSION

Although exemplary methods, devices, systems, etc., have been described in language specific to structural features and/or methodological acts, it is to be understood that the subject matter defined in the appended claims is not necessarily limited to the specific features or acts described. Rather, the specific features and acts are disclosed as exemplary forms of implementing the claimed methods, devices, systems, etc.

The invention claimed is:

1. A method comprising:
   receiving an electrocardiogram signal of cardiac electrical activity after delivery of electrical energy to the heart;
   rectifying the received electrocardiogram signal to produce a rectified electrocardiogram signal;
   acquiring at least a first result from a test using said received electrocardiogram and at least a second result from a test using said rectified cardiogram signal
   based at least in part on a combination of said first and second results, deciding whether the delivered electrical energy resulted in non-capture, capture or fusion.

2. The method of claim 1 wherein the electrical energy comprises energy associated with a pacing pulse to pace a ventricle of the heart.

3. The method of claim 1 wherein the electrical energy comprises energy associated with a pacing pulse for cardiac resynchronization therapy.

4. The method of claim 3 wherein the cardiac resynchronization therapy includes bi-ventricular pacing.

5. The method of claim 1 wherein the receiving receives the signal during an acquisition window.

6. The method of claim 5 wherein the acquisition window comprises a duration greater than approximately 40 ms.

7. The method of claim 1 wherein the rectifying rectifies the signal with respect to an analysis window.

8. The method of claim 7 wherein the analysis window comprises a time segment greater than approximately 40 ms.

9. The method of claim 1 wherein the deciding comprises using a table stored in memory of an implantable cardiac therapy device.

10. The method of claim 1 further comprising adjusting a cardiac pacing therapy based at least in part on the deciding.

11. An implantable device comprising:
    a processor;
    memory;
    circuitry to acquire cardiac electrograms;
    circuitry to rectify cardiac electrograms to create rectified cardiac electrograms; and
    control logic programmed to perform a first test using acquired electrocardiograms to acquire at least a first result and to perform a second test using said rectified cardiograms to acquire at least a second result and to decide whether capture, fusion or non-capture occurred in response to delivery of electrical energy to the heart based at least in part on a combination of the at least first and second results.

12. The implantable device of claim 11 further comprising a table stored in the memory and control logic to use the table to decide whether capture, fusion or non-capture occurred.

\* \* \* \* \*